(12) United States Patent
Spector

(10) Patent No.: US 7,084,389 B2
(45) Date of Patent: Aug. 1, 2006

(54) HAND HELD LED DEVICE

(76) Inventor: Donald Spector, 641 Fifth Ave., New York, NY (US) 10022

( * ) Notice: Subject to any disclaimer, the term of this patent is extended or adjusted under 35 U.S.C. 154(b) by 324 days.

(21) Appl. No.: 10/241,620

(22) Filed: Sep. 11, 2002

(65) Prior Publication Data

US 2004/0046108 A1    Mar. 11, 2004

(51) Int. Cl.
*G01J 1/04*    (2006.01)

(52) U.S. Cl. .............................. 250/227.13; 250/227.11
(58) Field of Classification Search ........... 250/227.13, 250/227.11, 216; 340/815.45, 815.49; 345/179, 345/180; 362/118, 119, 120; 607/88, 89; 606/9

See application file for complete search history.

(56) References Cited

U.S. PATENT DOCUMENTS

| | | | |
|---|---|---|---|
| 5,464,436 A | 11/1995 | Smith | 607/89 |
| 6,265,984 B1 * | 7/2001 | Molinaroli | 340/815.4 |
| 6,267,779 B1 * | 7/2001 | Gerdes | 607/89 |
| 6,306,160 B1 * | 10/2001 | Nidetzky | 607/89 |

OTHER PUBLICATIONS

Nasa Light Emitting Diode Medical Applications From Deep Space to Deep Sea, CP552, Space Technology and Applications International Forum, Jul. 2001.

* cited by examiner

*Primary Examiner*—Que T. Le
(74) *Attorney, Agent, or Firm*—Diehl Servilla LLC; Glen M. Diehl

(57) ABSTRACT

A hand held device is provided which contains at least one light emitting diode (LED) and is useful for the elimination of microorganisms as well as therapeutic treatment by light. A method of treatment and a kit are also disclosed.

19 Claims, 1 Drawing Sheet

HAND HELD LED DEVICE

FIELD OF THE INVENTION

This invention relates to a hand held LED device useful for the elimination or destruction of a wide variety of microorganisms, particularly harmful bacteria. It has also been found to be useful for the therapeutic treatment of several conditions existing in a patient

BACKGROUND ART

In the early years prior to the present invention, light emitting diodes (LED) did not produce light of sufficient intensity for many applications since they required a lot of power and in some instances extra cooling. Moreover, the typical life estimates of high output ultraviolet LED's was so short as to render them unsatisfactory for many uses. More recently, however, due in part to the advances made by the NASA Marshall Space flight Center and others, the technology relating to LED's has advanced dramatically. The present day LED's have become extremely powerful, cold to the touch and require very little energy.

Accordingly, light emitting diodes are now finding a wide variety of applications in both industrial and medical fields. For instance the newer LED's are now capable of destroying a wide variety of microorganisms, particularly bacteria which cause skin infections including staph, strep and the like. LED's have also been found to be useful in the destruction of the small pox virus, anthrax and the like.

Much of the published experimental work done by NASA with LED's relates to the affects of LED's on cells, muscle and bone since it had been observed that normal wound healing and cell growth are negatively affected by diminished gravity as is encountered in space. It has been observed that the applications of light therapy with the use of LED's significantly improved wound healing and cell and bone growth of astronauts on long term space missions.

Another area of technology in the medical field is the use of LED's in photodynamic therapy where an injected photosensitizer such as in cancer therapy, concentrates in a tumor, and when activated by a light source, can destroy the tumor.

Prior to the advance in LED technology, low level laser therapy had been used for performing therapy on patients particularly for the management and symptomatic relief of pain The low level laser therapy could reach deep into tissues and yet without harm to the tissues However, the combined wavelengths of light which are optional for wound healing cannot be efficiently produced and the size of wounds that can be treated by lasers is severely limited. Hence, LED's offer an effective alternate to lasers for many applications, including pain therapy. LED's are safe, non-invasive, drug free and therapeutic. It is believed that LED treatment stimulates natural physiological changes in the cells of a patients' body and helps to relieve pain naturally.

Although the use of ultra violet light for the sterilization of microorganisms was not practical up to the present due to the estimated limited life span of high output ultraviolet light emitting diodes, more recently technology has been developed high power ultra violet emitting diodes which have much longer spans. For example, it is now possible to have systems of 500 milliamps as opposed to the lower earlier systems of 30 milliamps.

Accordingly, the interest in developing method for sterilization of air and surfaces, including the treatment of human tissue, with LED's has increased markedly.

However, prior to the present invention, the devices presently used were somewhat cumbersome and tied to a fixed energy source which limited their portability. The present invention, therefore, has provided a portable, hand held device which can be obtained in the form of a kit and useful for a variety of applications.

It is therefore an object of the present invention to provide a portable, hand-held ultra-violet LED device which is useful in the destruction of microorganisms, and in particular, harmful bacteria. The device is also useful in a wide variety of therapeutic treatments. Another object of this invention is to provide a device which is hand-held and has its own independent energy source. A still further object is to provide a device which can be used to destroy bacteria that can cause pimples, boils, infections, and the like. Another aspect of this invention is to provide a hand-held LED device which emits a strong ultra-violet light source capable of penetrating through several layers of skin to destroy infectious bacteria. A still further object is to provide a hand held device which contains restraints to avoid accidental activation of the LED or unnecessary exposure to emitted light. Another object of this invention is to provide a device which contains a timer to limit the interval that the device is on. A still further object is to provide methods for utilizing the device of the present invention for the destructions of microorganisms and the treatment of various patient conditions. Another object is to provide a kit comprised of the device, preferably in the shape of a pen, battery, battery recharger and goggles for eye protection.

These and other objects will readily become apparent to those skilled in the art in light of the teachings herein set forth.

SUMMARY OF THE INVENTION

In its broad aspects, the present invention is directed to a hand held device containing at least one light emitting diode (LED) which is useful both for the destructions of microorganisms and for therapeutic purposes. The device being comprised of an enclosure having:

(a) at least one unidirectional light emitting diode (LED); disposed so as to emit light from the device and having a child proof protective means to prevent unintentional exposure to light emission;

(b) a rechargeable power source to activate the diode;

(c) a child proof switch assembly for engaging the power source to activate the diode; and (d) a timer to control the time interval in which light is emitted from the device.

In addition to the hand held device, the present invention is also directed to a method for using the device for elimination of microorganism and for the therapeutic treatment of patents. A kit is also provided which contains the device, power source, battery recharger and goggles for eye protection

BRIEF DESCRIPTION OF THE DRAWINGS

The device of the present invention will be better understood by reference to the drawings wherein.

DESCRIPTION OF THE PREFERRED EMBODIMENT

Figure 1:
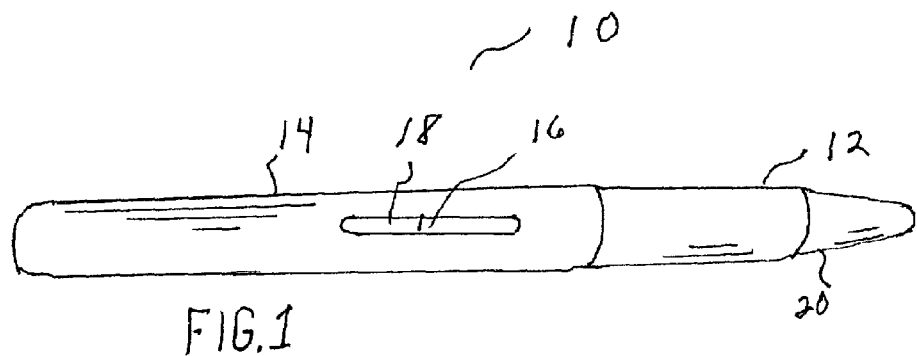
FIG. 1 is a perspective view of a hand-held, light emitting diode device in the shape of a pen useful for the destruction of microorganism.

Referring to the drawings, and more particularly to FIG. 1, the device 10 of the present invention is shown in the shape and approximate size of a pen having a barrel containing zone 12 which contains one or more light emitting diodes, zone 14, which contains the rechargeable power source, switch assembly 16 which has child proof restraints to prevent inadvertent activation of the device; timing means 18 to control and deactivate the device after a set time interval; and zone 20 from which the light is emitted in a unidirectional manner and which also contains child proof restraint means to prevent accidental light emission.

Figure 2:
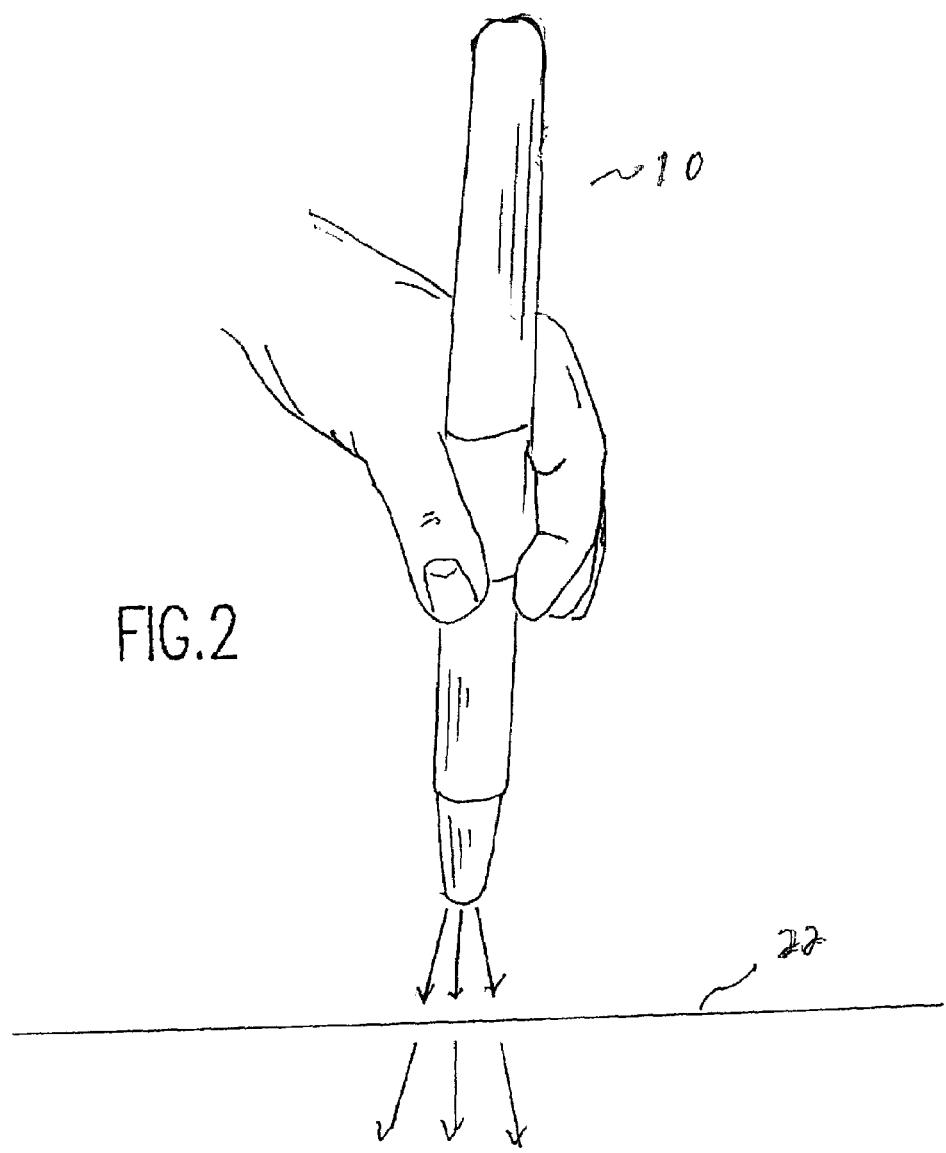
FIG. 2 illustrates the hand-held device of FIG. 1 and depicts it being held by a medical technician or physician for the treatment of microorganisms on a surface.

FIG. 2 depicts a physician or technician holding the device of this invention and directing the light to a surface 22 which could contain bacteria or could be the skin of a patient in need of treatment, for example, of an infection. Under the skillful hands of a physician or surgeon, the device can be employed for treating infections in the oral cavity, or other areas of a patients' body.

As indicated above, low level laser technology has in the past been employed for the therapeutic management a relief of pain in humans. For example, in U.S. Pat. No. 5,464,436, which issued Nov. 7, 1995, there is described a method of treating the external skin layer of a patient with a laser source which emits a laser light having a wave-length between 800 nm and 870 nm and at a level of 1 joule/cm$^2$ for each treatment cycle. It is indicated in this patent that while laser light of conventional systems can penetrate skin layers and cause injury to a patient, the use of a low level laser light therapy (LLLT) can reach into deep tissues to provide beneficial effects without doing harm to the tissue. In contract, the device of the present invention does not employ a laser source and due to the advances in LED technology is believed to be much safer and as efficient.

In practice it has been found that the device of the present invention provides wavelengths in the ultra violet range of about from 200 to 450 nanometers and higher, and energy levels of up to 35,000 microwatt seconds/cm$^2$, which are necessary to eliminate or destroy most microorganisms such as bacteria, spores, algae and viruses. Most bacteria can be destroyed at ultra violet energies of from about 3,000 to about 5,000 microwatt-seconds/cm$^2$ while mold spores may require energies in the 20,000 to 35,000 mW-seconds/cm$^2$.

In contrast to the commercial systems for ultra violet light sterilizations which are costly and difficult to maintain, LED technology has become of particular interest since systems which use this technology are at least as efficient and can operate for much longer periods of time than in the past.

In addition to its use in the destruction of microorganisms and for therapeutic applications, the device of the present invention is also useful in photodynamic therapy for activating photosensitzers. Improvements in semiconductor technology has greatly increased the light output of LED chips and has rendered them particularly attractive for various applications. For example, aluminum-gallium-arsenide is an excellent semiconductor and LEDs which have been manufactured from such composition are particularly attractive for use the absorption spectrum of certain photosensitizes such as lutetium texaphyrin and benzophorphyrin derivatives which are currently finding use in the treatment of brain tumors.

While it is preferred that the enclosure for the power source and LED be pen-like in shape for ease of handling as depicted in FIG. 2, it can be fabricated in other configurations as well. As shown in FIG. 1 the power source is preferably located in the rear section which can be threadably attached to the other section and easily removed when the batter power source needs recharging. Alternatively, the section containing the battery can have a lid opening allowing for a recharger to be temporarily connected to the battery without its removal from the enclosure.

The battery and the recharger are commercially available items. The battery will, of course, have sufficient power to provide the necessary energy levels indicated above for activation of the LED, and for the destruction of microorganisms as well as for therapeutic treatment.

The particular diodes employed in the device of the present inventions can be selected from a variety of crystals or chips depending upon the particular wave length desired A wide variety of inorganic electroluminescent compounds can be used as the light emitting diode. These compounds, or phosphors, are commercially available in crystal form. When exposed to an electrical current they fluoresce at different wavelengths depending upon the particular chemical composition of the phosphor and in many instances the kind of impurities present in, or added to, the phosphors.

Typical phosphors include but are not limited to, crystal compounds such as cadmium selenide, zinc sulfide, cadmium sulfide, mercury sulfide, zinc sulfide doped with copper, complexes of chromium, lithium and germanium oxides, complexes of zinc, cadmium, and selenium, yttrium oxysulfide and the like.

Of more recent interest are some of the organometallic compounds which are electroluminescent and in some instances may be competitive with the inorganic compounds presently in use as LED's.

Although the device of the present invention is deemed to be safer and at least as efficient as devices which employ lasers, it is not entirely without danger and reasonable cautions must be followed in its use. The device should only be used by technicians or medical personnel who have been trained in its use and who wear proper eye protection.

Accordingly, to maximize safety the device of the present invention has restraints on both the switch assembly and the point where light is emitted. Several known child proof features or a combination of features can be employed to prevent accidental or unauthorized activation of the device. For example, it may be necessary to twist one section of the pen-shaped device while simultaneously pressing down on the switch assembly to allow the device to be activated or a shutter mechanism to be opened to permit light emission.

Additionally, the device includes a built-in timer which will allow the device when activated to emit light for a predetermined interval and then automatically turn off. Such timing devices are known in the art and are commercially available.

While the invention is directed to a hand held device which is free of a connection to an external power source, in some instances it may be desirable to be able to plug in the device to an external source via an appropriate extension cord.

Although the invention has been illustrated by the preceding disclosure, it is not to be construed as being limited to the materials employed herein, but rather, the inventions pertains to the generic area as hereinbefore disclosed. Various modifications and embodiments thereof can be made without departing from the spirit and scope thereof.

What is claimed is:

1. A hand held device containing at least one light emitting diode (LED) which is useful for both destruction of microorganisms and therapeutic treatments, said device being comprised of an enclosure having:
  a) at least one unidirectional light emitting diode (LED) disposed so as to emit light from said enclosure and having child proof protective means to prevent exposure to light emission;
  b) a rechargeable power source;
  c) a switch assembly with child proof restrains to engage said power source and activate said light emitting diode; and
  d) a timer to control and limit the time intervals in which light is emitted from said light emitting diode.

2. The device of claim 1 wherein the emitted light is ultra-violet.

3. The device of claim 1 wherein the device is in the shape of a pen.

4. The device of claim 1 wherein LED is at least one crystal selected from the group consisting of cadmium selenide, zinc sulfide, cadmium sulfide, mercury sulfide, zinc sulfide doped with copper, complexes of chromium, lithium and germanium, and complexes of zinc, cadmium and selenium.

5. The device of claim 1 wherein the source of the light emitted is an aluminum gallium arsenide crystal.

6. A method for the destruction of microorganisms which comprises exposing said microorganisms to the light emitted from the device of claim 1 for a period of time sufficient to destroy said microorganisms.

7. The method of claim 6 wherein the microorganisms are bacteria.

8. The method of claim 6 wherein the microorganisms are viruses.

9. The method of claim 6 wherein the microorganisms are spores.

10. A method of providing light therapy to a patient in need of such therapy which comprises exposing such patient a therapeutically, effective amount of light emitted from the device of claim 1.

11. The method of claim 10 wherein said patient had previously been administered a photosensitive pharmaceutically acceptable composition which is activated by sound light therapy.

12. The method of claim 10 wherein the therapy needed by said patent is therapy for pain.

13. The method of claim 10 wherein said patient needs therapy for a wound healing.

14. The method of claim 10 wherein the therapy needed by said patient is therapy for an infection.

15. A kit comprised of
  (1) at least one device of claim 1,
  (2) at least one rechargeable battery,
  (3) a battery recharger, and
  (4) a pair of goggles.

16. The kit of claim 15 wherein the device emits ultra-violet light.

17. The kit of claim 15 wherein the device emits infrared light.

18. A device of claim 1 wherein said light emitting diode is capable of emitting light at energy levels capable of destruction of microorganisms.

19. The device of claim 1, wherein the light emitting diode emits energy in the range of about 3,000 to about 35,000 mW-seconds/cm$^2$.

* * * * *